US00PP08058P

United States Patent [19]

VandenBerg

[11] Patent Number: Plant 8,058

[45] Date of Patent: Dec. 8, 1992

[54] CHRYSANTHEMUM PLANT NAMED VOLARE

[75] Inventor: Cornelis P. VandenBerg, Salinas, Calif.

[73] Assignee: Yoder Brothers, Inc., Barberton, Oreg.

[21] Appl. No.: 651,001

[22] Filed: Feb. 5, 1991

[51] Int. Cl.[5] ..... A01H 5/00

[52] U.S. Cl. ..... Plt./74.1

[58] Field of Search ..... Plt./74

*Primary Examiner*—James R. Feyrer

*Attorney, Agent, or Firm*—Foley & Lardner

[57] ABSTRACT

A Chrysanthemum plant named Volare particularly characterized by its flat capitulum form; daisy capitulum type; light purple ray floret color; diameter across face of capitulum of 80 to 83 mm when fully opened when grown as a single stem spray cut mum; flowering response in Salinas under normal temperatures of 49 to 52 days after start of short days and of 63 to 70 days in Bogota, Colombia; plant height of 91 to 99 cm when grown in Salinas with 14 long days prior to start of short days compared to 104 to 112 cm when grown in Bogota with 17 to 21 long days prior to start of short days; peduncle length of the first lateral of 13 to 15 cm when grown in Salinas, and 13 to 18 cm when grown in Bogota; peduncle length of the fourth laterial of 18 cm when grown in Salinas, and 18 to 23 cm when grown in Bogota; and excellent tolerance to low night temperatures for bud initiation and flower development.

3 Drawing Sheets

1

The present invention comprises a new and distinct cultivar of Chrysanthemum, botanically known as *Dendranthema grandiflora,* and referred to by the cultivar named Volare.

Volare, identified as 87-512013, was originated from a cross made by Cornelis P. VandenBerg in a controlled breeding program in Salinas, Calif., in 1986.

The female parent of Volare was the cultivar identified as Oreo, disclosed in U.S. Plant Pat. No. 6,882, and described as a purple flat daisy cut spray mum. A more detailed description of Oreo can be found in attached Chart A, in which certain characteristics of Volare are compared with the same characteristics of Oreo.

The male parent of Volare was an unnamed seedling, identified as 83-715009, and described as a white flat daisy spray cut mum, having a flowering response to short days of 55 to 64 days in Salinas, Calif., and 80 days in Bogota, Colombia, a plant height of 69 to 89 cm with 7 to 14 long days prior to start of short days, and a peduncle length of 10 to 13 cm of the first lateral and 15 to 18 cm of the fourth lateral, with both height and peduncle length being measured in Salinas. The male parent was tested only twice in Colombia and was discarded from the Colombian program in November 1985, because of very slow flowering response, and was discarded completely from all programs in September 1987.

Volare was discovered and selected as one flowering plant within the progeny of the stated cross by Cornelis P. VandenBerg on January 1988, in a controlled environment in Salinas, Calif.

The first act of asexual reproduction of Volare was accomplished when vegetative cuttings were taken from the initial selection in March 1988 in a controlled environment in Salinas, Calif., by technicians working under supervision of Cornelis P. VandenBerg.

Horticultural examination of controlled flowerings of successive plantings has shown that the unique combination of characteristics as herein disclosed for Volare are firmly fixed and are retained through successive generations of asexual reproduction.

2

Volare has not been observed under all possible environmental conditions. The phenotype may vary significantly with variations in environment such as temperature, light intensity and daylength.

The following observations, measurements and comparisons describe plants grown in Salinas, Calif., and in Bogota, Colombia, under greenhouse conditions which approximate those generally used in commercial greenhouse practice. The low temperature tolerance was determined in repeated flowerings in Bogota, Colombia, with an average minimum low night temperature inside the greenhouse during our trials ranging from 6.3 to 10.0 degrees Celsius.

The following traits have been repeatedly observed and are determined to be basic characteristics of Volare, which, in combination, distinguish this Chrysanthemum as a new and distinct cultivar:

1. Flat capitulum form.
2. Daisy capitulum type.
3. Light purple ray floret color.
4. Diameter across face of capitulum of 80 to 83 mm when fully opened, when grown as a single stem spray cut mum.
5. Flowering response in Salinas under normal temperatures is 49 to 52 days after start of short days. Flowering response in Bogota, Colombia under temperatures of minimum 6.3 degrees Celsius night and maximum 29 degrees Celsius day is 63 to 70 days.
6. Plant height is 91 to 99 cm when grown in Salinas with 14 long days prior to start of short days; height is 104 to 112 cm when grown in Bogota with 17 to 21 long days prior to start of short days.
7. Peduncle length of the first lateral at flowering after removing the apical bud without growth regulator applications is 13 to 15 cm when grown in Salinas, and 13 to 18 cm when grown in Bogota. Peduncle length of the fourth lateral at flowering is 18 cm when grown in Salinas, and 18 to 23 cm when grown in Bogota.

8. Excellent tolerance to low night temperatures for bud initiation and flower development.

The accompanying photographic drawings show typical inflorescence and leaf characteristics of Volare, with the colors being as nearly true as possible with illustrations of this type.

Sheet 1 is a color photograph of Volare grown as a single stem spray cut mum.

Sheet 2 is a black and white photograph of three views of the inflorescence of Volare.

Sheet 3 is a black and white photograph showing the upper and under sides of the leaves of Volare at 3 stages of development (mature, intermediate and immature). In sheets 2 and 3 a measuring tape in centimeters has been included.

Of the commercial cultivars known to the inventor, the most similar in comparison to Volare is the female parent cultivar Oreo. Reference is made to attached Chart A, which compares certain characteristics of Volare to the same characteristics of Oreo.

Similar traits are capitulum form and type, spray formation and low night temperature tolerance. Plant height is comparable for both cultivars. Volare has a slightly lighter ray floret color, a larger flower diameter, a slower flowering response in Bogota, and longer peduncle length of the first lateral when compared with Oreo.

When compared with the male parent, Volare has a much faster flowering response and a greater plant height. In addition, the ray floret color of the male parent is white, while the ray floret color of Volare is light purple.

In the following description color references are made to The Royal Horticultural Society Colour Chart. The color values were determined on plant material grown as a single stem cut mum in Salinas, Calif. on Sep. 12, 1990.

Classification:

*Botanical.*—*Dendranthema grandiflora* cv Volare.

*Commercial.*—Daisy spray cut mum.

INFLORESCENCE

A. Capitulum:

*Form.*—Flat.

*Type.*—Daisy.

*Diameter across face.*—80 to 83 mm when fully opened.

B. Corolla of ray florets:

*Color (general tonality from a distance of three meters).*—Light purple.

*Color (upper surface).*—75D.

*Color (under surface).*—75D.

*Shape.*—Straight, slightly ribbed.

C. Corolla of disc florets:

*Color (mature).*—14B.

*Color (immature).*—144B.

D. Reproductive organs:

*Androecium.*—Present on disc florets only; moderate pollen.

*Gynoecium.*—Present on both ray and disc florets.

PLANT

A. General appearance:

*Height.*—91 to 99 cm when grown in Salinas with 14 long days prior to start of short days, and 104 to 112 cm when grown in Bogota with 17 to 21 long days prior to start of short days.

B. Foliage:

*Color (upper surface).*—147A.

*Color (under surface).*—147B.

*Shape.*—See photograph.

CHART A

COMPARISON OF VOLTARE AND OREO

| Characteristic | Voltare | Oreo |
|---|---|---|
| Ray floret color | Light purple | Purple |
| Capitulum form and type | Flat daisy | Flat daisy |
| Diameter across face of capitulum | 80 to 83 mm | 70 to 73 mm |
| Flowering response | | |
| in Salinas | 49 to 52 days | 47 to 58 days |
| in Bogota | 63 to 70 days | 58 to 63 days |
| Plant height: | | |
| 14 long days Salinas | 91 to 99 cm | 91 to 102 cm |
| 17-21 long days Bogota | 104 to 112 cm | 94 to 112 cm |
| Peduncle length: | | |
| 1st lateral Salinas | 13 to 15 cm | 8 to 13 cm |
| 4th lateral Salinas | 18 cm | 15 to 18 cm |
| 1st lateral Bogota | 13 to 18 cm | 10 to 15 cm |
| 4th lateral Bogota | 18 to 23 cm | 13 to 20 cm |
| Spray formation | Terminal | Terminal |
| Low night temperature tolerance | Excellent | Excellent |

COMPARISONS MADE OF PLANTS GROWN AS SINGLE STEM SPRAY CUT MUMS IN SALINAS, CALIFORNIA AND IN BOGOTA, COLUMBIA

I claim:

1. A new and distinct Chrysanthemum plant named Volare, as described and illustrated.

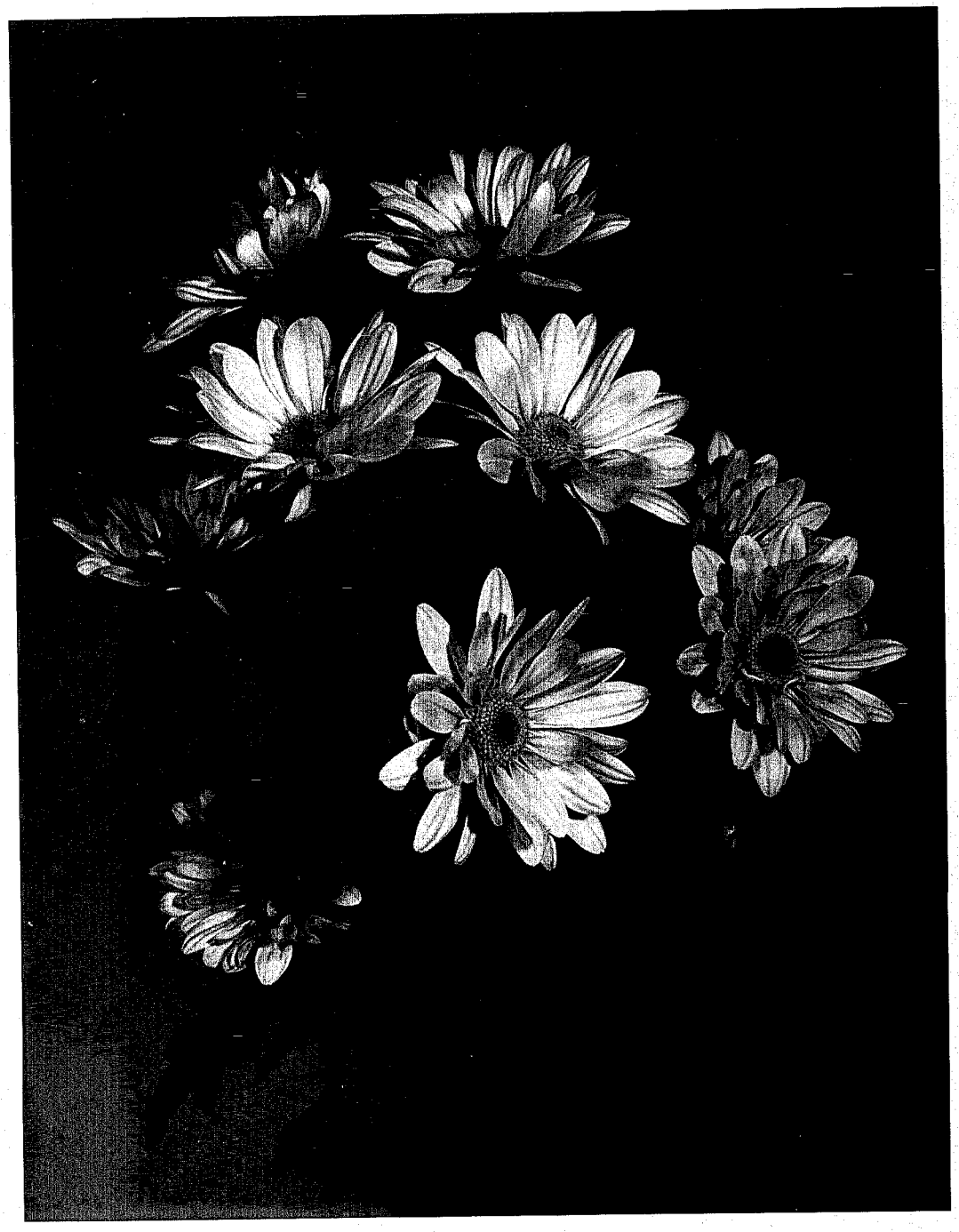

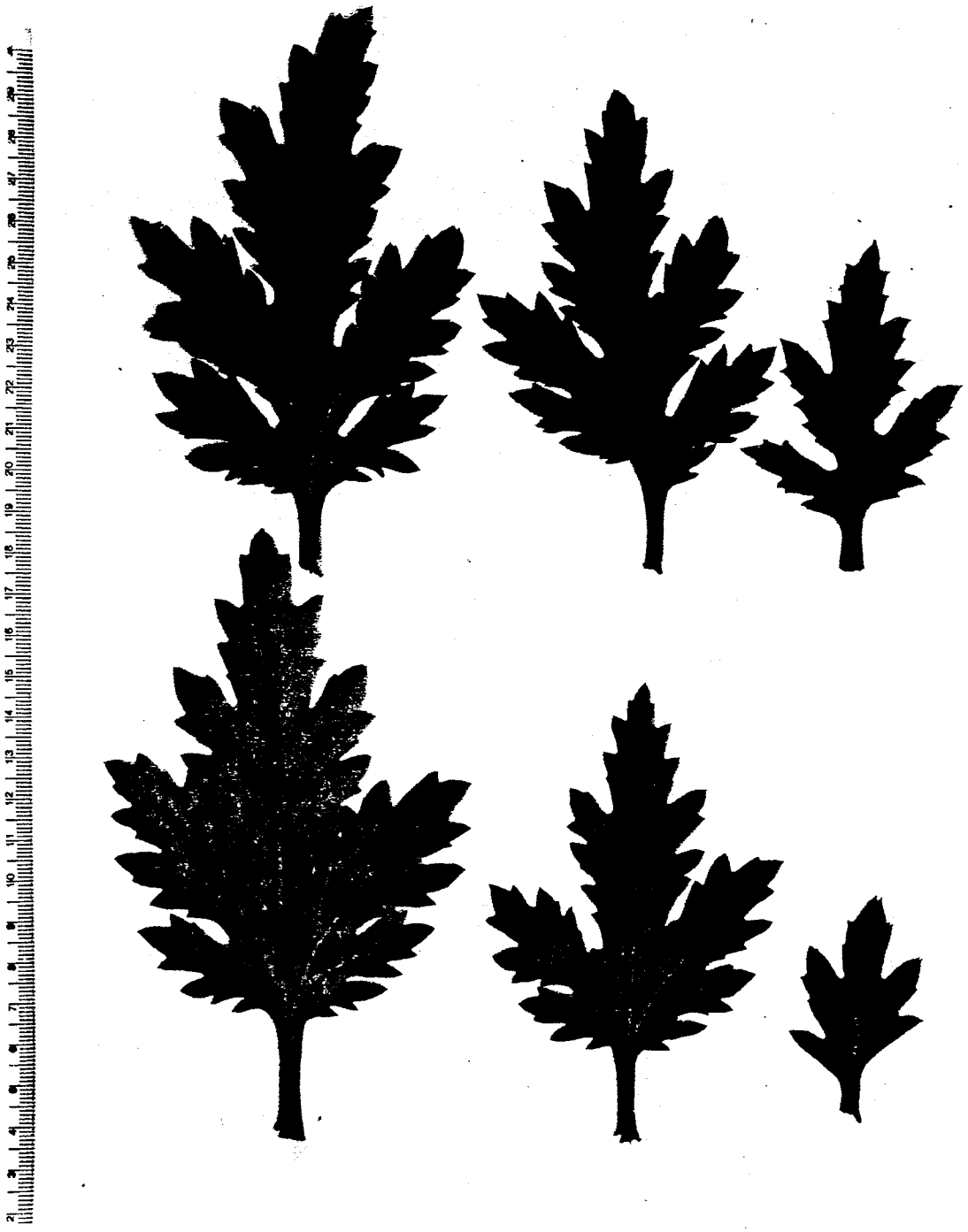

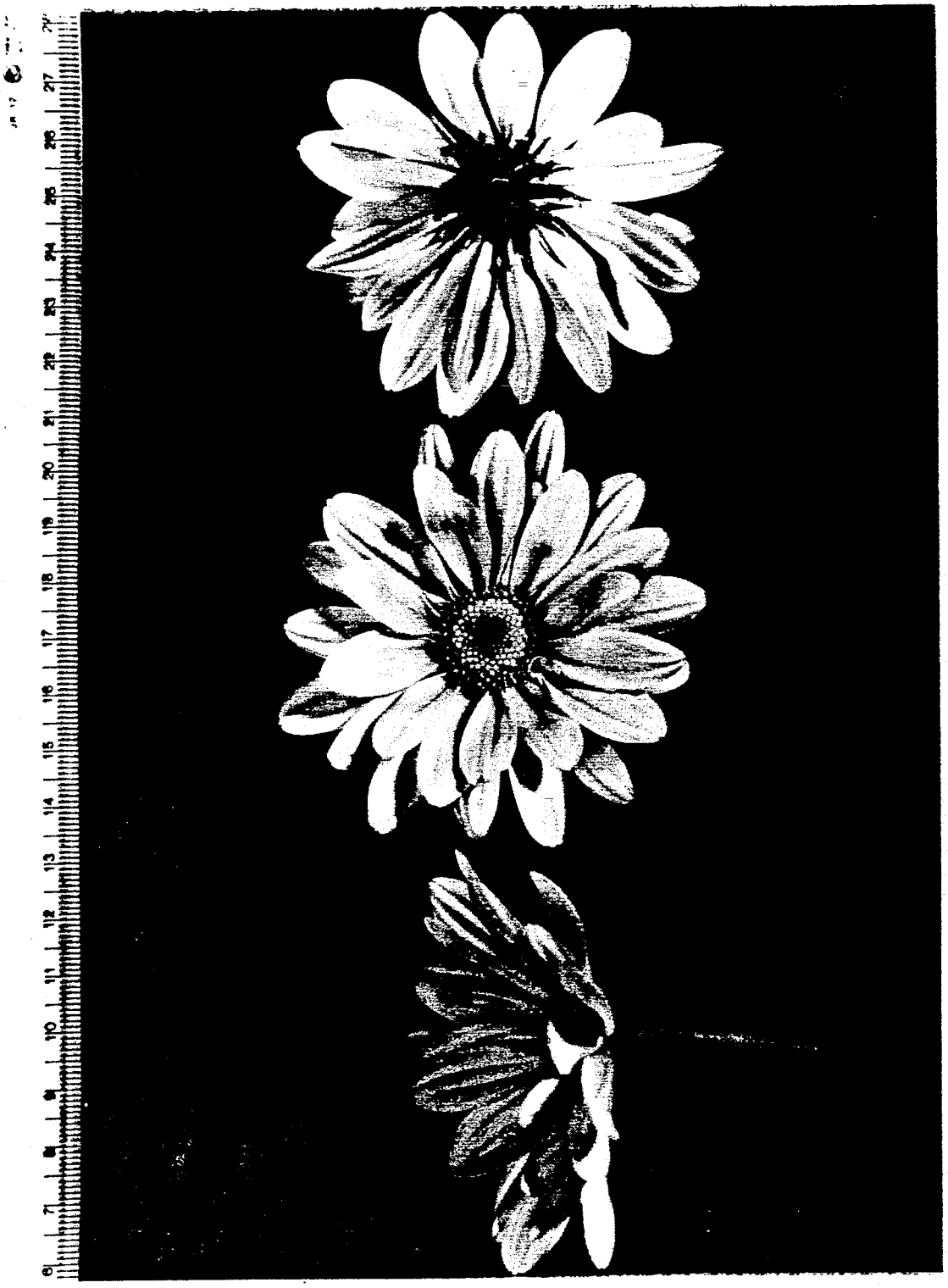

* * * * *